United States Patent
Robinson et al.

(10) Patent No.: US 10,369,010 B2
(45) Date of Patent: Aug. 6, 2019

(54) EXPANDABLE INTER-BODY FUSION DEVICES AND METHODS

(71) Applicant: Spectrum Spine IP Holdings, LLC, Atlanta, GA (US)

(72) Inventors: James C Robinson, Atlanta, GA (US); John E Pendleton, Atlanta, GA (US)

(73) Assignee: SPECTRUM SPINE IP HOLDINGS, LLC, Atlanta, GA (US)

( * ) Notice: Subject to any disclaimer, the term of this patent is extended or adjusted under 35 U.S.C. 154(b) by 365 days.

(21) Appl. No.: 14/777,494

(22) PCT Filed: Mar. 17, 2014

(86) PCT No.: PCT/US2014/030862
§ 371 (c)(1),
(2) Date: Sep. 15, 2015

(87) PCT Pub. No.: WO2014/145995
PCT Pub. Date: Sep. 18, 2014

(65) Prior Publication Data
US 2016/0030189 A1  Feb. 4, 2016

Related U.S. Application Data

(60) Provisional application No. 61/786,612, filed on Mar. 15, 2013.

(51) Int. Cl.
*A61F 2/44* (2006.01)
*A61F 2/30* (2006.01)
*A61F 2/46* (2006.01)

(52) U.S. Cl.
CPC .......... *A61F 2/447* (2013.01); *A61F 2/30744* (2013.01); *A61F 2/4611* (2013.01); *A61F 2/4684* (2013.01); *A61F 2002/30261* (2013.01); *A61F 2002/30266* (2013.01); *A61F 2002/30398* (2013.01); *A61F 2002/30509* (2013.01); *A61F 2002/30556* (2013.01); *A61F 2002/30579* (2013.01); *A61F 2002/30904* (2013.01); *A61F 2002/4475* (2013.01)

(58) Field of Classification Search
CPC ............................ A61F 2/4455; A61F 2/4465
USPC ..................................................... 623/17.16
See application file for complete search history.

(56) References Cited

U.S. PATENT DOCUMENTS

| | | |
|---|---|---|
| 5,683,394 A | 11/1997 | Rinner |
| 6,896,677 B1 | 5/2005 | Lin |
| 7,722,674 B1 | 5/2010 | Grotz |
| 8,292,958 B1 | 10/2012 | Bruffey et al. |
| 8,398,713 B2 | 3/2013 | Weiman |
| 8,888,853 B2 | 11/2014 | Glerum et al. |

(Continued)

*Primary Examiner* — Si Ming Ku
(74) *Attorney, Agent, or Firm* — FisherBroyles LLP; Anthony Dovale

(57) ABSTRACT

An expandable curved inter-body fusion device is presented. The expandable curved inter-body fusion device can have a first plate, a second plate, and an insert positioned substantially therebetween the first plate and the second plate. The first plate, the second plate, and the insert define an interior cavity. Moving the insert longitudinally with respect to the first and second plates increases or decreases the distance of the first plate with respect to the second plate, effectively expanding the inter-body fusion device and increasing the volume of the interior cavity.

12 Claims, 4 Drawing Sheets

(56) References Cited

U.S. PATENT DOCUMENTS

| | | |
|---|---|---|
| 8,888,854 B2 | 11/2014 | Glerum et al. |
| 8,894,711 B2 | 11/2014 | Varela |
| 8,894,712 B2 | 11/2014 | Varela |
| 8,926,704 B2 | 1/2015 | Glerum et al. |
| 9,549,824 B2 * | 1/2017 | McAfee ................ A61F 2/447 |
| 2004/0087947 A1 | 5/2004 | Lim et al. |
| 2006/0122701 A1 | 6/2006 | Kiester |
| 2006/0129244 A1 * | 6/2006 | Ensign ................ A61F 2/4455 623/17.16 |
| 2008/0234687 A1 | 9/2008 | Schaller et al. |
| 2010/0204795 A1 * | 8/2010 | Greenhalgh ....... A61B 17/7064 623/17.16 |
| 2010/0292796 A1 * | 11/2010 | Greenhalgh ....... A61B 17/8858 623/17.11 |
| 2011/0307065 A1 | 12/2011 | Hsu et al. |
| 2011/0319997 A1 | 12/2011 | Glerum et al. |
| 2012/0029637 A1 | 2/2012 | Ragab et al. |
| 2012/0059470 A1 | 3/2012 | Weiman |
| 2012/0226357 A1 | 9/2012 | Varela |
| 2012/0232552 A1 * | 9/2012 | Morgenstern Lopez ................ A61B 18/1487 606/45 |
| 2012/0310349 A1 | 12/2012 | Gordon et al. |
| 2013/0023994 A1 | 1/2013 | Glerum |
| 2013/0085572 A1 | 4/2013 | Glerum et al. |
| 2013/0103153 A1 | 4/2013 | Blackwell et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2015/0012097 A1 | 1/2015 | Ibarra et al. |
| 2015/0012098 A1 | 1/2015 | Eastlack et al. |
| 2015/0012101 A1 | 1/2015 | Glerum et al. |
| 2015/0073553 A1 | 3/2015 | Barreiro |
| 2015/0112438 A1 | 4/2015 | McLean |

* cited by examiner

EXPANDABLE INTER-BODY FUSION DEVICES AND METHODS

FIELD OF THE INVENTION

This invention relates generally to spinal surgery, and more particularly to devices and methods for stabilization of the spine in association with placement of an expandable inter-body construct for inter-body fusion or the like.

BACKGROUND OF THE INVENTION

Damage or disease that affects the spinal disc within an individual's spinal column may lead to neurologic impairment with possible permanent damage to the surrounding tissue. Maintaining proper anatomic spacing and lordosis within the spine is critical to ensuring continued functionality of the surrounding tissue and for the spinal column, the spinal cord and nerve roots and therefore, avoidance of long term serious neurological impairment.

Typically, spinal implants that are used as a spacer type of device have a fixed overall length and are implanted without the ability to adjust the degree of expansion or curvature without using multiple insertion instrumentation. Some of the known procedures for introducing spinal implants comprise Anterior Lumbar Inter-body Fusion ("ALIF"), Lateral Lumbar Inter-body Fusion ("LLIF"), Posterior Lumbar Inter-body Fusion ("PLIF"), Oblique Lumbar Inter-body Fusion ("OLIF"), Direct Lateral Fusion ("DLIF"), Transforaminal Lumbar Inter-body Fusion ("TLIF"), and the like. A need remains for a multipurpose instrument to be used to implant a spacer type of implant that allows the surgeon to minimize the size of the surgical incision, facilitate the operative technique and decrease patient morbidity.

SUMMARY

Presented herein is an expandable inter-body fusion device, or implant, for use in spinal surgery. In one aspect, the expandable inter-body fusion device comprises a first plate, a second plate, and an insert positioned substantially therebetween the first plate and the second plate. The first plate, the second plate, and the insert define an interior cavity. In one aspect, moving the insert longitudinally with respect to the first and second plates increases or decreases the distance of the first plate with respect to the second plate, effectively expanding the inter-body fusion device and increasing the volume of the interior cavity.

It is contemplated that this technology can be used for a variety of implants used for a variety of spinal procedures. These procedures include, but are not limited to OLIF (anterior or posterior), DLIF, PLIF, TLIF, ALIF, and LLIF. So, depending upon the procedure and point of insertion for the implant, the geometry of the implant will differ.

In an exemplified aspect, at least one of the first plate and the second plate define at least one graft window that is in communication with the interior cavity.

Also presented herein is a method of using an expandable cage during an inter-body fusion procedure. In one aspect, the method comprises accessing the desired disc space, choosing the correct insert size with the appropriate height and angle, inserting the expandable inter-body fusion device into the desired area in the disc space, expanding the expandable inter-body fusion device from the first non-expanded position to the second expanded position, and securing the insert to the first and second plates. An additional step of packing the interior cavity via the aperture in the trailing end of the expandable inter-body fusion device with bone fusion material either prior to or after expansion is also contemplated.

Related methods of operation are also provided. Other apparatuses, methods, systems, features, and advantages of the expandable inter-body fusion device and the method of its use will be or become apparent to one with skill in the art upon examination of the following figures and detailed description. It is intended that all such additional apparatuses, methods, systems, features, and advantages be included within this description, be within the scope of the expandable inter-body fusion device and the method of its use, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

DESCRIPTION OF THE INVENTION

Figure 1:
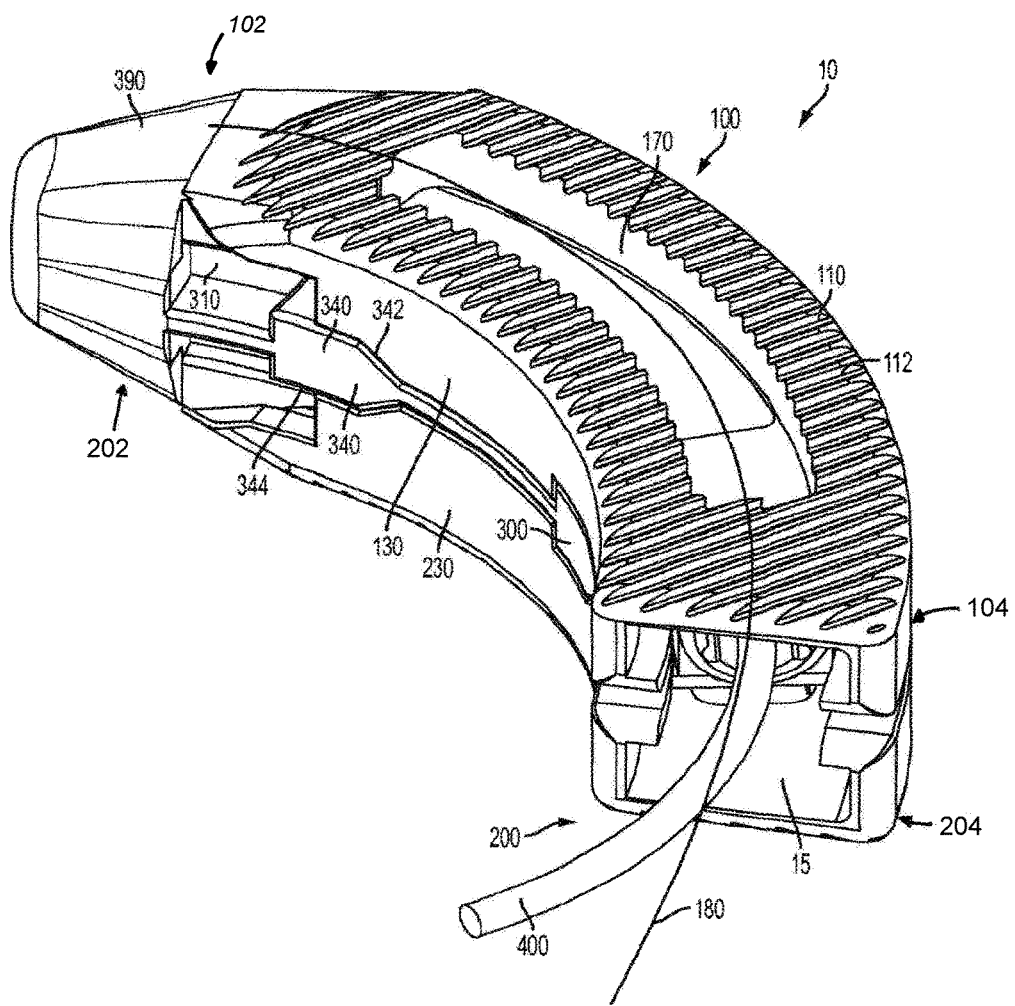
FIG. 1 is a perspective view of one aspect of an expandable inter-body fusion device with curved first and second plates and a flexible insertion tool.
Figure 2:
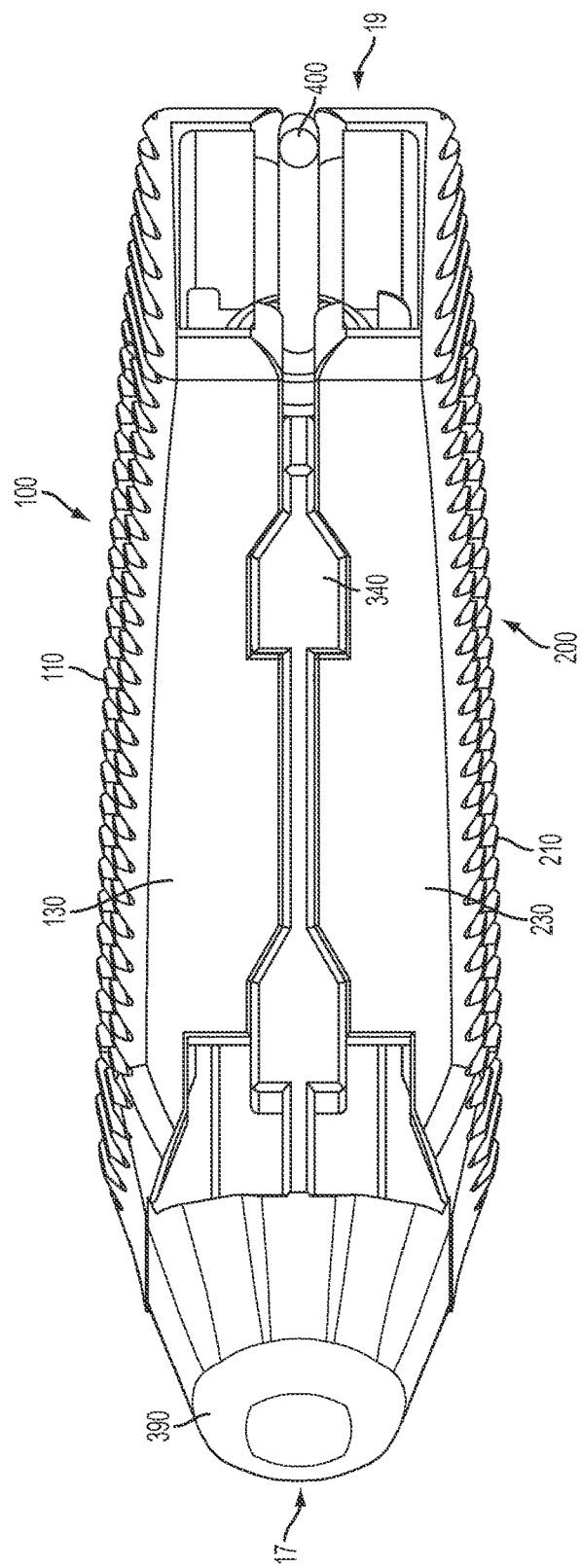
FIG. 2 is a side elevational view of the expandable inter-body fusion device of FIG. 1 in the first unexpanded position.
Figure 3:
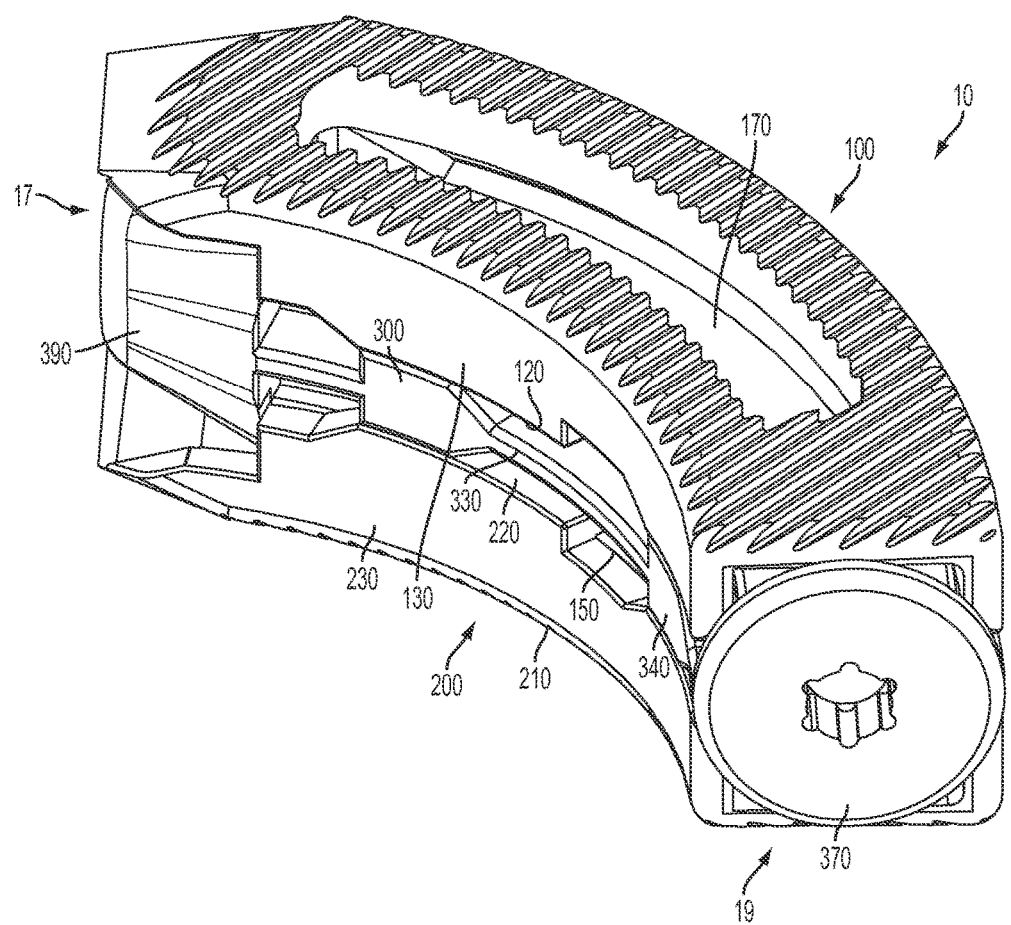
FIG. 3 is a perspective view of the expandable inter-body fusion device of FIG. 1 in the second expanded position.
Figure 4A:
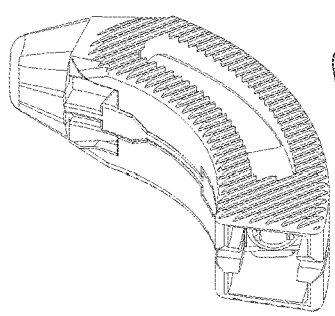
FIG. 4 is a series of perspective views of a curved expandable inter-body fusion device used in a TLIF approach.
Figure 4B:
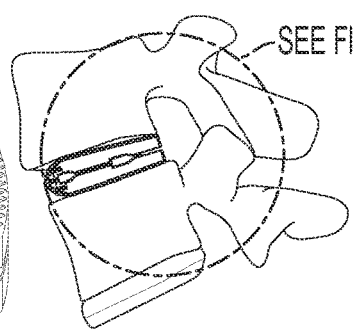
Figure 4C:
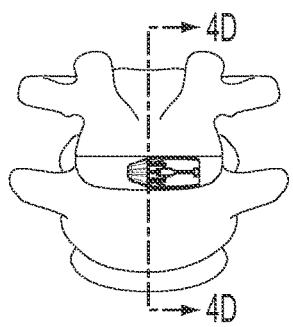
Figure 4D:
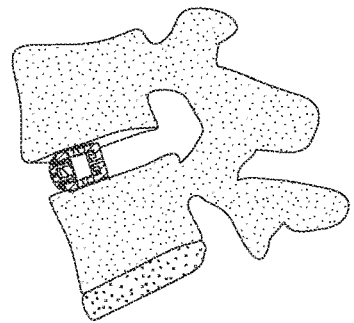
Figure 4E:
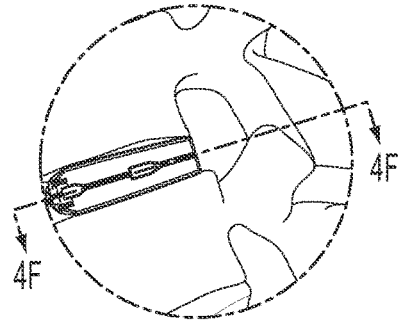
Figure 4F:
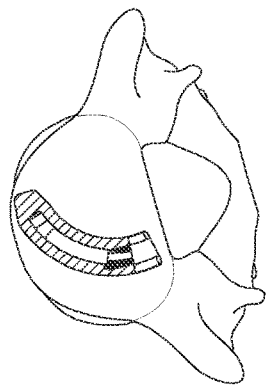
Figure 4G:
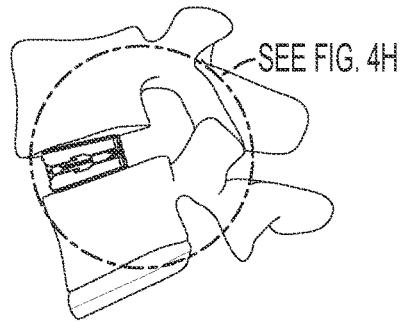
Figure 4H:
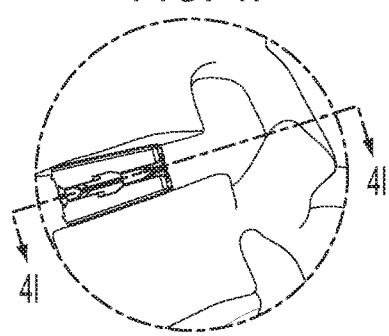
Figure 4I:
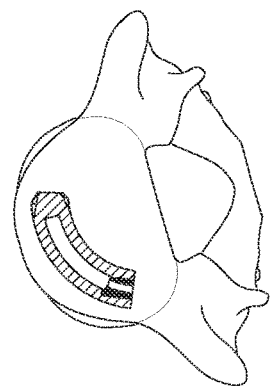

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "plate" includes aspects having two or more plates unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

Additionally, as used herein, relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

In one aspect, presented herein is an expandable inter-body fusion device 10 for use in spinal surgery, such as, but not limited to, ALIF, OLIF, TLIF, LLIF, PLIF, and DLIF procedures.

In one aspect, the expandable inter-body fusion device 10 comprises a first plate 100, a second plate 200, and an insert 300 positioned substantially therebetween the first plate 100 and the second plate 200. The first plate 100 has an upper bone contact surface 110 and an opposed first plate inner surface 120. The second plate 200 has a lower bone contact surface 210 and an opposed second plate inner surface 220. The first plate 100, the second plate 200, and the insert 300 define an interior cavity 15. In one aspect, moving the insert longitudinally with respect to the first and second plates increases the distance of the first plate with respect to the second plate, effectively expanding the inter-body fusion device and increasing the volume of the interior cavity 15.

At least one of the first or second plates has at least one longitudinal sidewall 130, 230 extending substantially from its inner surface. In one aspect, the longitudinal sidewall 130, 230 comprises two longitudinal sidewalls. In another aspect, the longitudinal sidewall(s) are positioned substantially near a peripheral edge 140, 240 of the first and/or second plate.

In one exemplified aspect, the insert 300 comprises a frame 310 with two longitudinal frame sides 310. In one aspect, a longitudinal rail 330 protrudes from the external surface of each of the longitudinal frame sides 310. Each of the longitudinal rails, in one aspect, comprises at least one ramp 340 having an incline surface 342 and a substantially flat surface 344. In another aspect, each of the longitudinal rails 330 comprises a plurality of ramps. Correspondingly, in one aspect, the longitudinal sidewalls of the first plate substantially align with the longitudinal sidewalls of the second plate. Each set of substantially aligned longitudinal sidewalls (one longitudinal sidewall from the first plate and one from the second plate) define at least one hollow 150 to complimentarily accept a ramp 340, such that, in a first unexpanded position, each of the ramps is positioned substantially within a hollow 150. In the first unexpanded position, each longitudinal sidewall 130, 230 can be positioned substantially near or in contact with the respective longitudinal rail 330. This is the position in which the expandable inter-body fusion device is to be inserted between the adjacent vertebrae.

To expand the expandable inter-body fusion device 10 into the second expanded position, the insert is moved longitudinally, moving the ramps into contact with a portion of at least one of the longitudinal sidewalls, causing the aligned longitudinal sidewalls of the first and second plates to separate by traveling up the inclined surfaces until they are separated and supported by the flat surfaces of the ramps. In the second expanded position, portions of the longitudinal sidewalls are supported by the load bearing properties of the flat surfaces of the ramps. As one skilled in the art can appreciate, the amount of separation achievable is determined by the height of the ramp.

In an exemplified aspect, at least one of the first plate and the second plate define at least one graft window 170, 270 that is in communication with the interior cavity. The at least one graft window 170 defined in the first plate can also be at least partially overlying the at least one graft window 270 of the second plate, thereby permitting bone growth therethrough. In another aspect, the upper bone contact surface 110 of the first plate 100 comprises ridges 112 for frictionally engaging the first vertebra. As can be appreciated, the lower bone contact surface 210 of the second plate can also comprise ridges 212 to frictionally engage the second vertebra.

In one aspect, the device can also comprise an endcap 370 configured to engage the insert. A portion of the endcap 370 extends past the peripheral edge of the aperture such that, when engaged with the insert, the endcap prevents the insert from moving back toward the leading end. As one skilled in the art can appreciate, the moving back of the insert toward the leading end would result in the unwanted moving of the inter-body fusion device from the second expanded position to the first unexpanded position. In this aspect, the trailing end of the insert 300 can be threaded to facilitate the complimentary threading of the endcap. Additionally, the threaded trailing end can also be used to engage the distal end of the insertion tool (not shown) and permit the movement of the insert with respect to the first and second plates. In this aspect, the leading end of the insert can comprise a tapered nose 390.

As shown in the figures, the first plate and the second plate are curved from the leading end 102, 202 to the trailing end 104, 204, as shown in FIG. 1. As such, the insert is complimentarily curved. The upper bone contact surface of the curved expandable inter-body fusion device may be angled with respect to the lower bone contact surface from either the leading end to the trailing end or about the center line of curvature 180, or both, depending about the direction of insertion. It is contemplated that, once the curved expandable inter-body implant is positioned and expanded, it is the upper bone contact surface 110 is angled with respect to the lower bone contact surface substantially only in lordosis.

In one aspect, the curved expandable inter-body fusion device 10 is expanded by pulling the insert from the leading end 17 toward the trailing end. Due to the curvature, it may be difficult to use an elongate and straight insertion tool. In an exemplified aspect, a flexible tool can be used. For example, a flexible driver with a distal end configured for engagement with a portion of the insert may be used. Other devices, such as a cable or wire are also contemplated.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A curved expandable inter-body fusion device, comprising:
   a first plate having an upper bone contact surface, an opposed first plate inner surface, a leading end, and a trailing end, wherein the first plate is curved from the leading end to the trailing end;
   a second plate having a lower bone contact surface, an opposed second plate inner surface, a leading end, and a trailing end, wherein the second plate is curved to substantially match the curve of the first plate;
   an insert positioned between the first plate and the second plate, wherein the insert is curved complimentary to the curve of the first and second plates; and
   a flexible insertion tool comprising a wire or cable and having a distal end configured for engagement with a portion of the insert and configured to directly pull the insert;
   wherein, the first plate, the second plate, and the insert define an interior cavity, and wherein pulling the flexible insertion tool moves the insert longitudinally with respect to the first and second plates and increases the distance of the first plate with respect to the second plate, effectively expanding the inter-body fusion device and increasing the volume of the interior cavity.

2. The curved expandable inter-body fusion device of claim 1, wherein at least one of the first and second plates has at least one longitudinal sidewall extending substantially from its inner surface.

3. The curved expandable inter-body fusion device of claim 2, wherein the at least one of the first and second plates comprises two longitudinal sidewalls.

4. The curved expandable inter-body fusion device of claim 1, wherein the insert comprises a frame with two longitudinal frame sides and a longitudinal rail, and wherein the longitudinal rail protrudes from an external surface of each of the longitudinal frame sides.

5. The curved expandable inter-body fusion device of claim 4, wherein each of the longitudinal rails comprises at least one ramp having an incline surface and a substantially flat surface.

6. The curved expandable inter-body fusion device of claim 5, wherein each of the longitudinal rails comprises a plurality of ramps.

7. The curved expandable inter-body fusion device of claim 5, wherein the first and second plates each have two longitudinal sidewall extending substantially from its inner surface, and wherein the longitudinal sidewalls of the first plate substantially align with the longitudinal sidewalls of the second plate, forming two sets of substantially aligned longitudinal sidewalls, and wherein each set of substantially aligned longitudinal sidewalls define at least one hollow to complimentarily accept a ramp of the plurality of ramps, such that, in a first unexpanded position, each ramp of the plurality of ramps is positioned substantially within a hollow.

8. The curved expandable inter-body fusion device of claim 5, wherein to expand the expandable inter-body fusion device into the second expanded position, the insert is moved longitudinally, moving the ramps into contact with a portion of at least one of the longitudinal sidewalls, causing the longitudinal sidewalls of the first and second plates to separate by traveling up the inclined surfaces until they are separated and supported by the flat surfaces of the ramps.

9. The curved expandable inter-body fusion device of claim 1, wherein at least one of the first plate and the second plate define at least one graft window that is in communication with the interior cavity.

10. The curved expandable inter-body fusion device of claim 9, wherein the first plate and the second plate define a graft window and, wherein the graft window defined in the first plate is at least partially overlying the graft window defined in the second plate, thereby permitting bone growth therethrough.

11. The curved expandable inter-body fusion device of claim 1, further comprising an endcap configured to engage the insert, wherein a portion of the endcap, when engaged, extends past a peripheral edge of an aperture in the trailing end of the expandable inter-body fusion device such that the endcap prevents the insert from moving back toward the leading end.

12. The curved expandable inter-body fusion device of claim 1 wherein the curved expandable inter-body fusion device is to be angled with respect to the lower bone contact surface from one of the leading end to the trailing end and the trailing end to the leading end, or about a center line of curvature.

* * * * *